US00PP36340P2

(12) United States Plant Patent
Wheeler et al.

(10) Patent No.: US PP36,340 P2
(45) Date of Patent: Dec. 31, 2024

(54) BLUEBERRY PLANT NAMED 'PE2103'

(50) Latin Name: *Vaccinium corymbosum*
Varietal Denomination: PE2103

(71) Applicant: BB IP Repository, LLC, Grand Juncion, MI (US)

(72) Inventors: Edmund J. Wheeler, Holland, MI (US); Bárbara Beatriz Ávila Lizana, Santiago (CL)

(73) Assignee: BB1P Repository, LLC, Grand Junction, MI (US)

( * ) Notice: Subject to any disclaimer, the term of this patent is extended or adjusted under 35 U.S.C. 154(b) by 0 days.

(21) Appl. No.: 18/739,956

(22) Filed: Jun. 11, 2024

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 5/08
See application file for complete search history.

*Primary Examiner* — Kent L Bell
(74) *Attorney, Agent, or Firm* — King IP Law; Joshua King

(57) ABSTRACT

'PE2103' is a new and distinct tetraploid southern highbush blueberry (*Vaccinium corymbosum* L.) plant adapted to a non-chill environment, upright growth habit, early production, and fruit that are large sized, firm and very good fresh market quality and storage ability.

6 Drawing Sheets

Latin name of the genus and species of the plant claimed: *Vaccinium corymbosum.*

Variety denomination: Blueberry plant named 'PE2103'.

BACKGROUND AND SUMMARY

Blueberries are a well-known fruit enjoyed by many throughout the world. One example of an existing, patented blueberry variety is 'Ventura', U.S. Plant Pat. No. 24,606. Another example of an existing, patented blueberry variety is 'BB14-232PT-2', U.S. Plant Pat. No. 35,026. Compared to 'Ventura', 'PE2103' is earlier blooming and has earlier maturing fruit than 'Ventura'. 'PE2103' has larger fruit size, is firmer and sweeter than 'BB14-232PT-2' (U.S. Plant Pat. No. 35,026).

'PE2103' originated as a seedling from a controlled cross pollination between 'STELLAR' (brandname for 'BB06-50FL-1', U.S. Plant Pat. No. 30,445) as the female (seed) parent and 'BB14-112PT-2' (U.S. Plant Pat. No. 35,671) as the male (pollen) parent. This cross was made in a field in Chao, Peru in May 2018. Seedlings were planted in a tropical environment in January 2021, and first fruit was evaluated in July 2021. 'PE2103' was selected for its early fruit ripening and outstanding fruit quality characteristics, excellent sweet and well-balanced flavor, firm texture, and large fruit size.

'PE2103' was asexually propagated by in vitro, via tissue culture in Chao, Peru in spring 2021, and 30 plants were planted in February 2022 in plots in the block trial test in Chao, Peru.

These plots have been observed during flowering and ripening each year, and no mutations or off-type plants have been observed. All the observed plants retained the characteristics of the original selection and reproduce true to type.

Time of fruit production in 'PE2103' is regulated by pruning date and environment conditions.

'PE2103' was selected in sandy soil and tested also under substrate soilless production.

Areas of adaptation include coast of Perú, or any tropical areas with no chill. It has not been tested in temperate zone areas yet.

'PE2103' differs from the parent 'STELLAR' (brandname for 'BB06-50FL-1' U.S. Plant Pat. No. 30,445) in that 'PE2103' is earlier ripening. 'PE2103' is a non-chill requirement variety and has upright growth habit. No chill requirement allows 'PE2103' to be grown in tropical environments as an evergreen plant. 'PE2103' differs from 'BB14-112PT-2' (U.S. Plant Pat. No. 35,671) in sweeter and firmer berries, with berry firmness from 200-250 gf/mm.

'PE2103' is a sweet, low acid, and firm genotype adapted to tropical non-chill environment. 'PE2103' does not require chill-hours for either budbreak or for fruit production since it does not develop endo-dormancy. 'PE2103' was selected in sandy soil and tested also under substrate soilless production.

It is a highly productive genotype with early maturity fruit, and very good fresh market quality and storage ability.

BRIEF DESCRIPTION OF THE PHOTOGRAPHS

FIG. 1 is a photograph of the whole plant of the Blueberry cultivar 'PE2103', showing mature plants during fruit production. Picture was taken in 2023 in Peru, Chao. Mature (two years old) plant.

DETAILED DESCRIPTION

Figure 1:
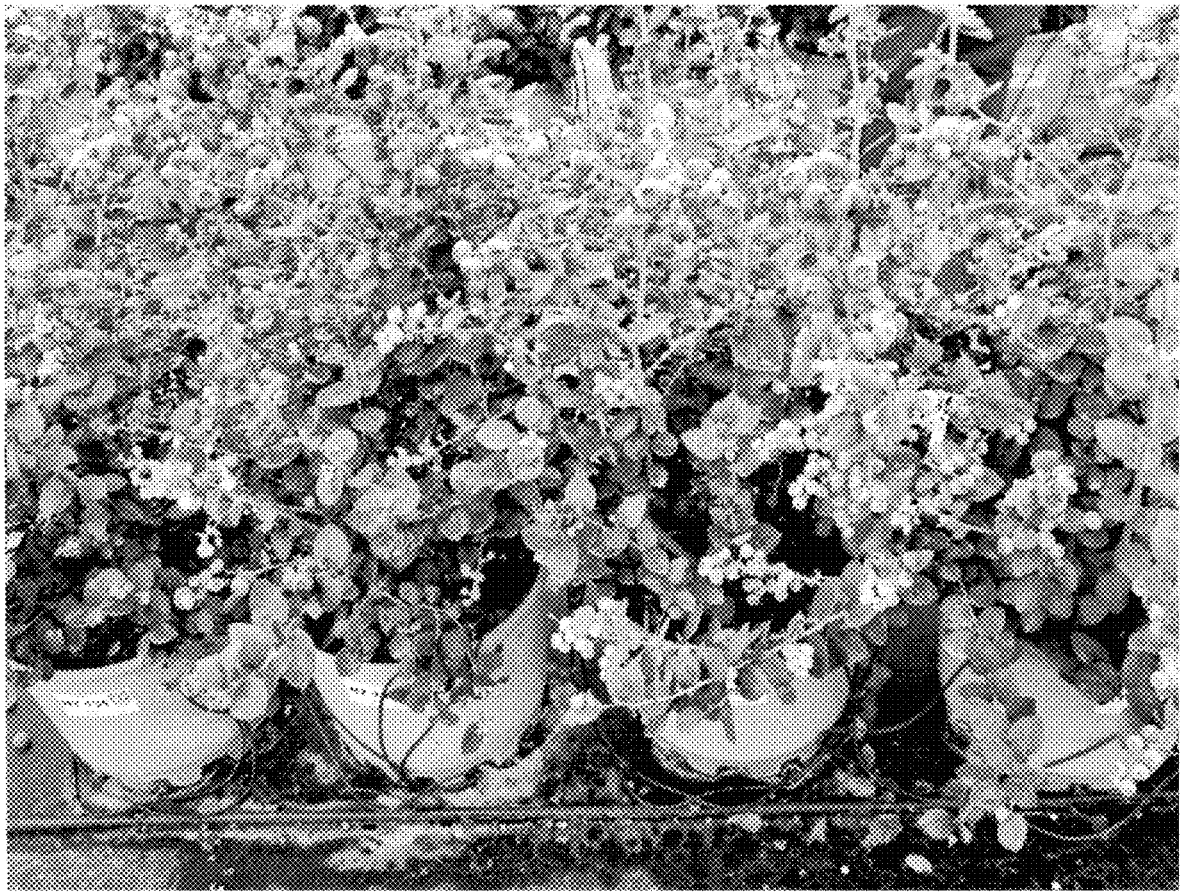
Figure 2:
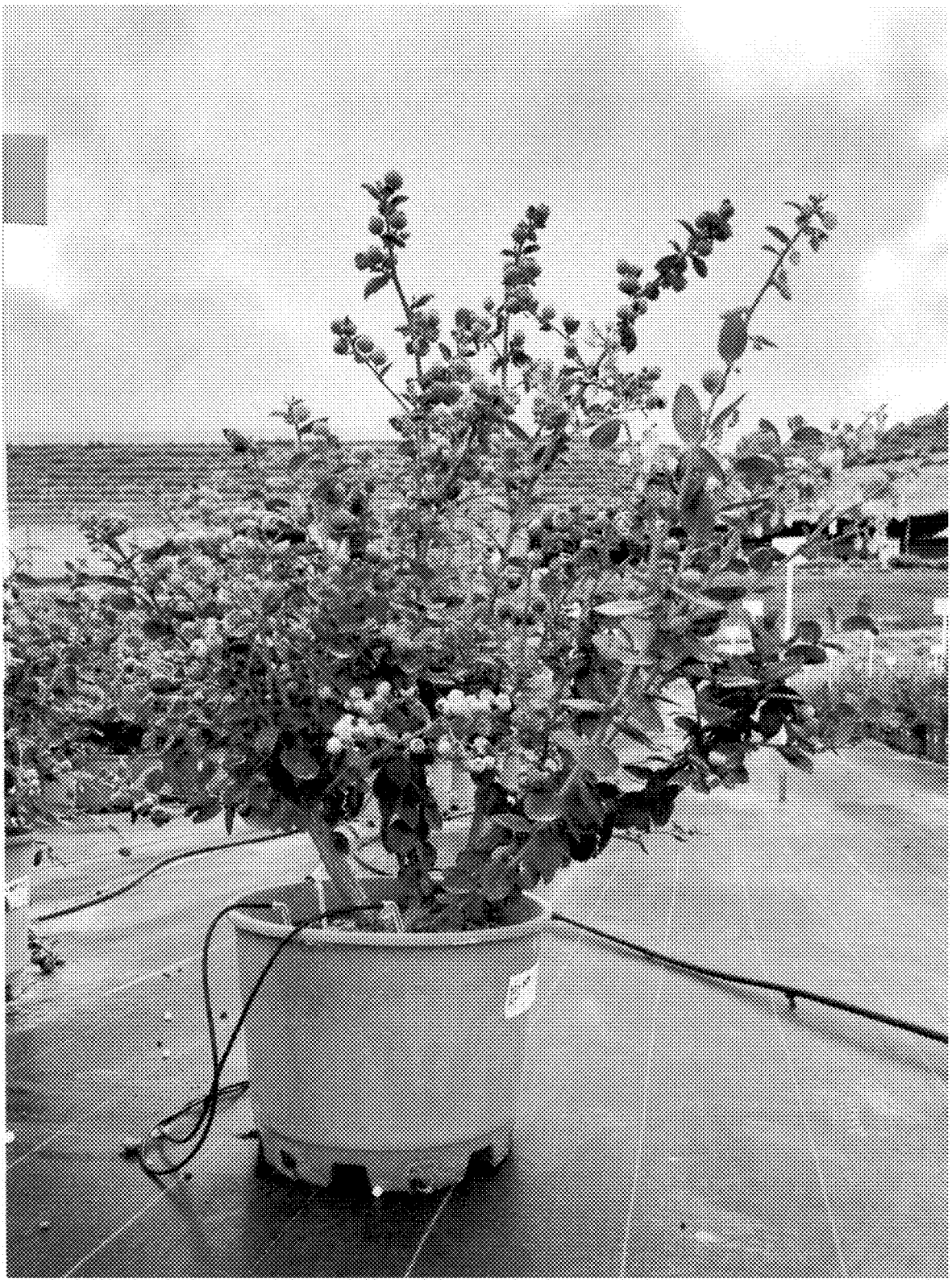
FIG. 2 is a photograph of the whole mature and individual plant (two years old) of Blueberry cultivar 'PE2103', showing plant habit, vigor, branching, unripe and ripe fruit.
Figure 3:
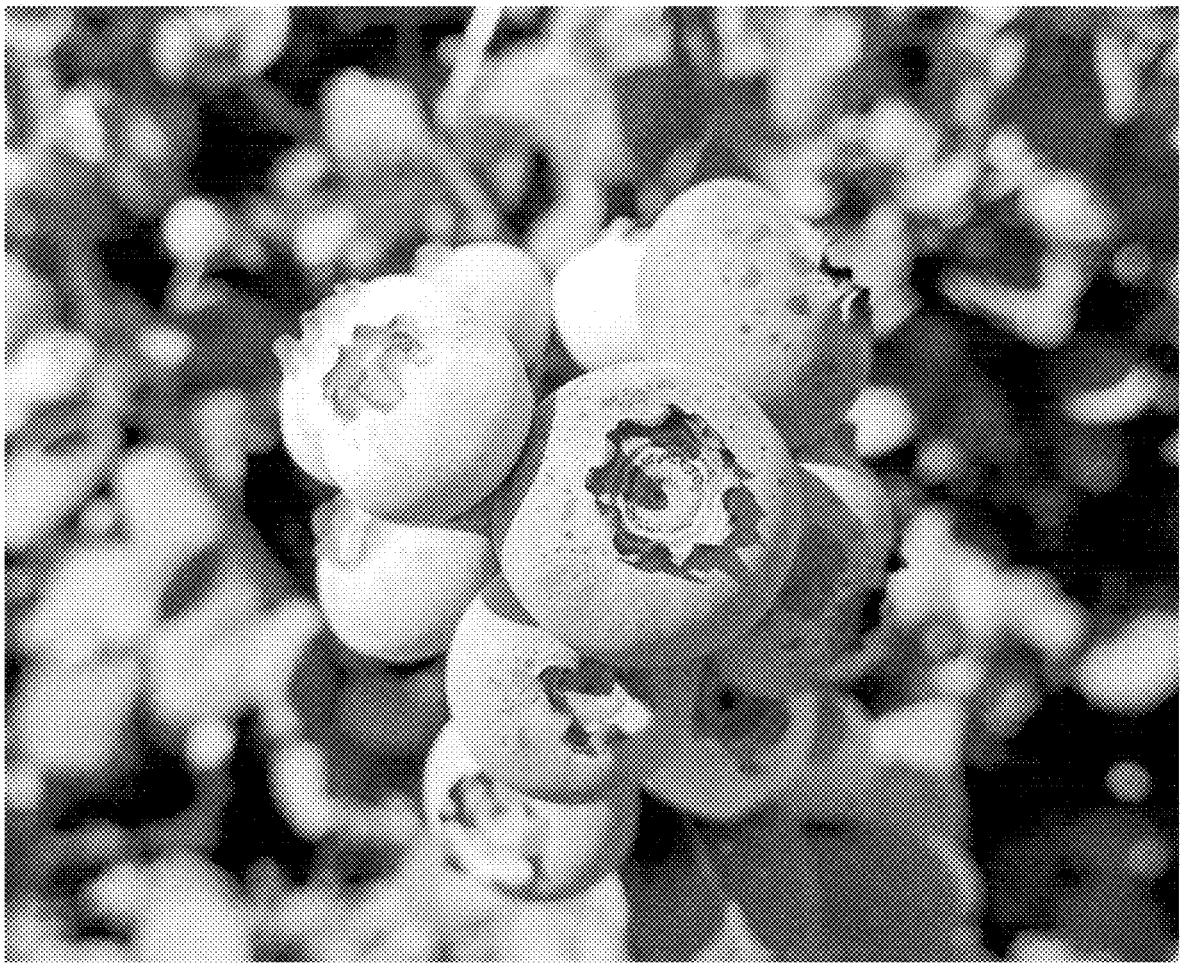
FIG. 3 is a close-up photograph of the Blueberry cultivar 'PE2103', showing a fruit cluster during fruit ripening. Picture shows crown size, color, and shape of unripe and ripe fruit.
Figure 4:
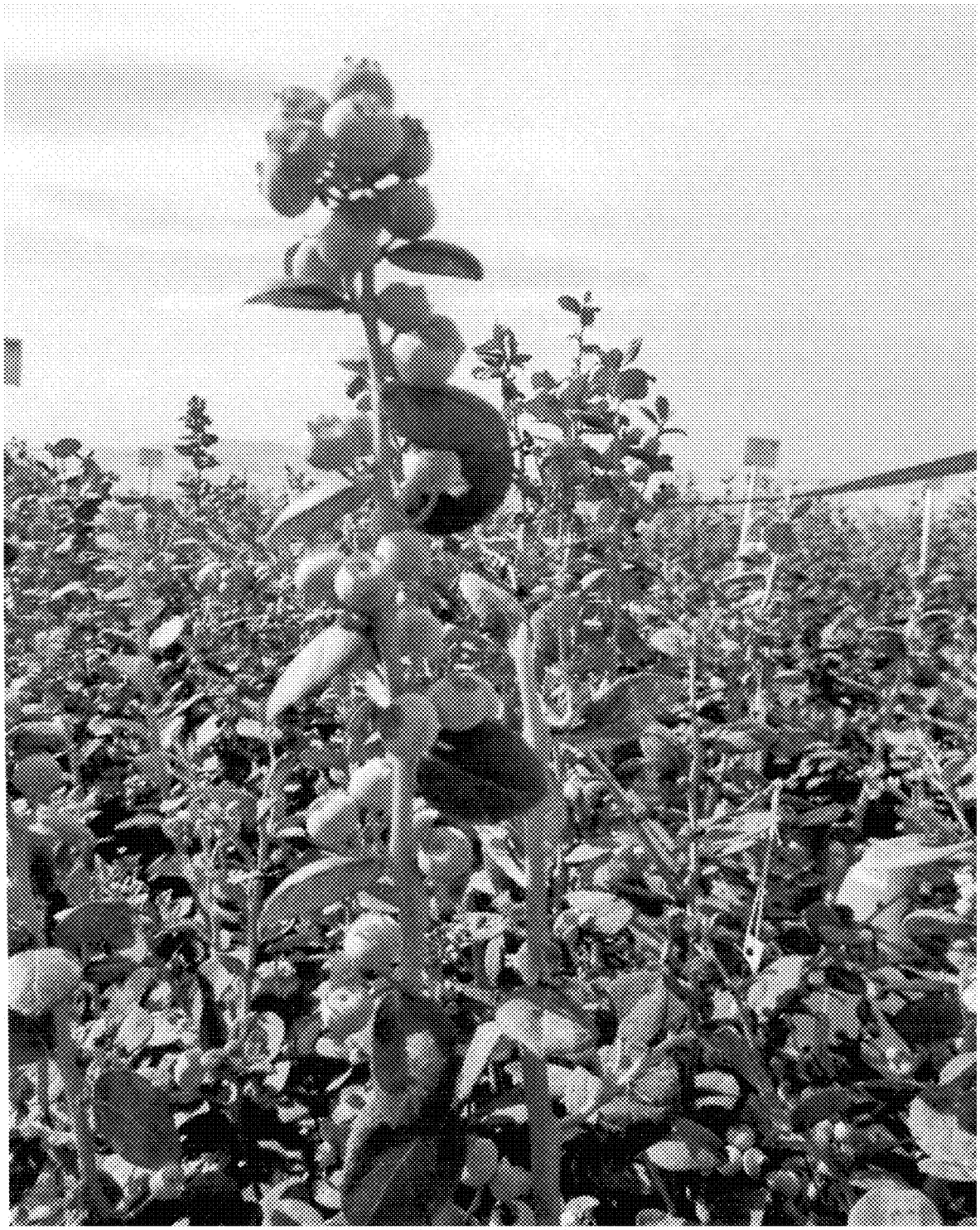
FIG. 4 is a photograph of the Blueberry cultivar 'PE2103', showing fruit distribution along the shoot, shoot color, leaf color and leaf shape.
Figure 5:
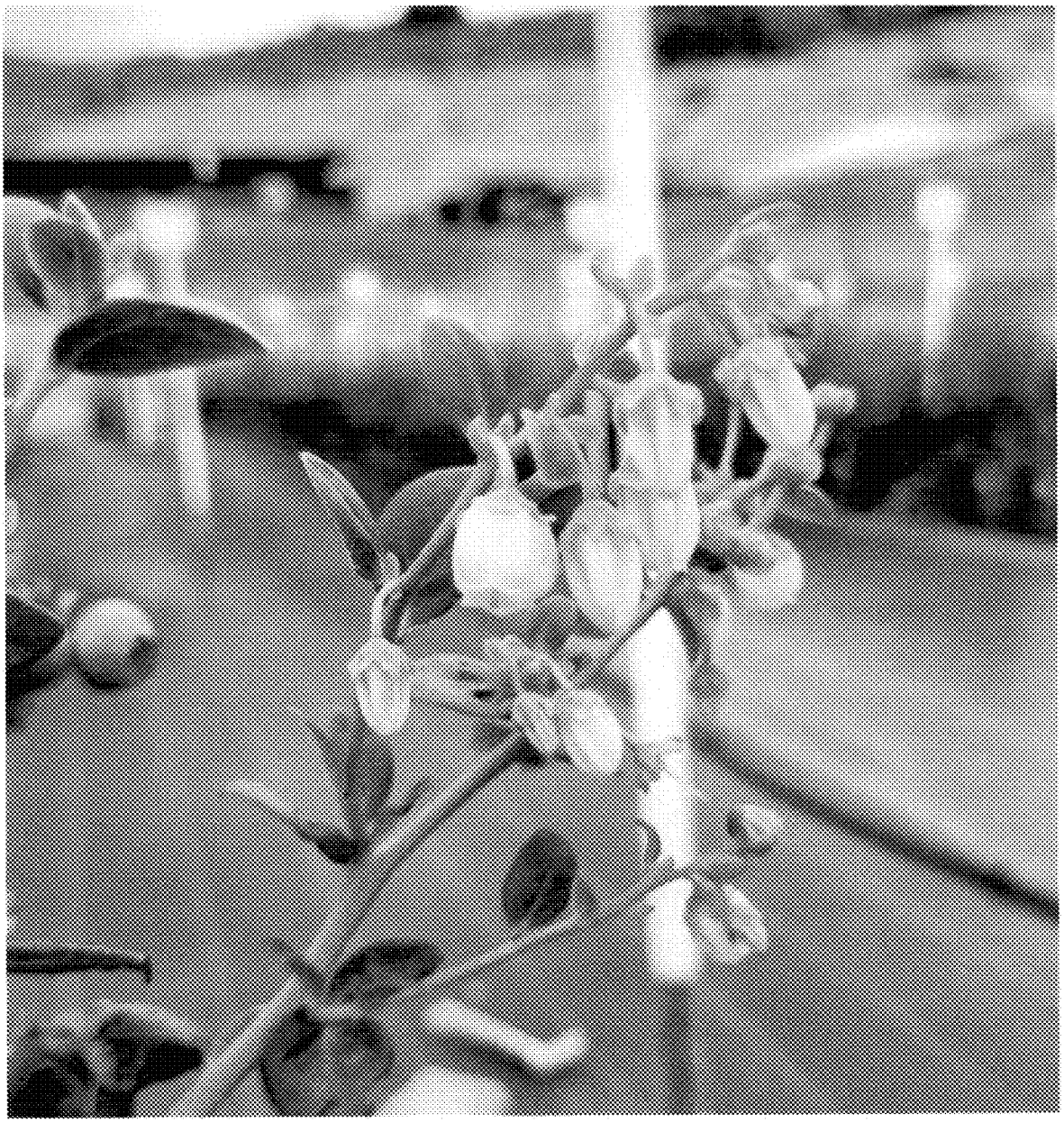
FIG. 5 is a close-up photograph of the Blueberry cultivar 'PE2103', showing a flower cluster, flower color and flower shape.
Figure 6:
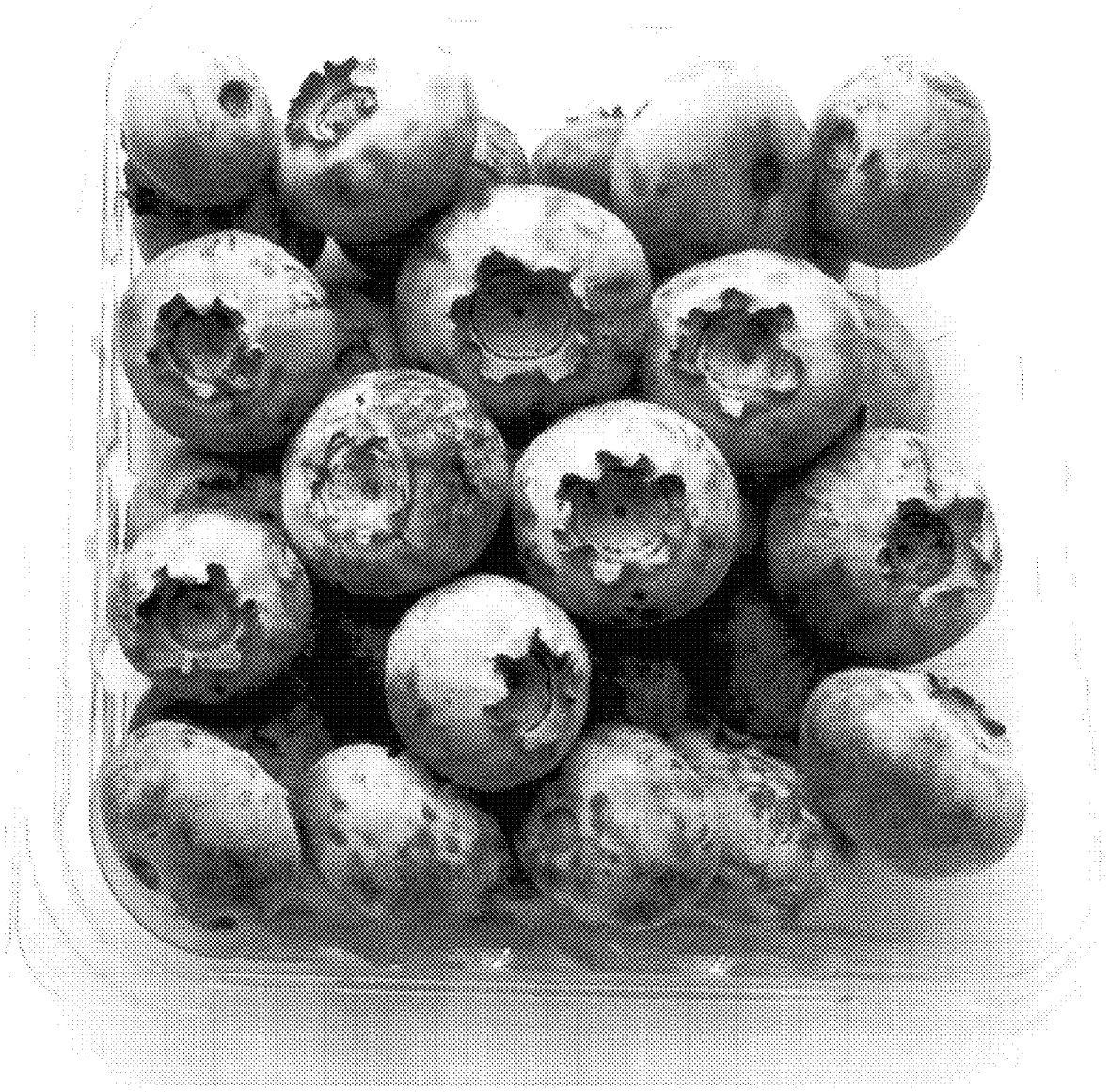
FIG. 6 is a is a close-up photograph of the Blueberry cultivar 'PE2103', showing harvest fruit, fruit color, fruit size and fruit shape.

The following detailed description sets forth distinctive characteristics of 'PE2103'. The data that define these characteristics were collected from asexual reproductions carried out in Chao, Peru (8° 35'12"S 78° 35'58"W), and will vary depending on time of year, location, annual temperate conditions, and weather, etc. Where dimensions, sizes, colors, and other characteristics are given, it is to be understood that such characteristics are approximations and averages.

The descriptions reported herein are based on the original selected individual bush and cloned plants planted in Chao, Peru and observed in successive years through 2022, 2023 and 2024 (2-3 year old mature plants). Laboratory analysis of fruit characteristics were done in Chao, Peru.

Color descriptions are based on The Royal Horticultural Society (R.H.S.) Colour Chart by The Royal Horticultural Society, London, Fifth Edition, 2007.

Firmness was measured with a FirmPro Fruit Firmness Tester.

Sugar content: was measured with Atago® refractometer.

Titratable acidity: was measured with a Mettler Toledo® Titrator.

Specific features of the variety:

Plant:

*Growth habit.*—Upright.
*Plant width.*—100 cm.
*Plant height.*—85 cm.
*Productivity.*—3.0-3.5 Kg mature plant.
*Cold hardiness/tolerance.*—Not tested.
*Chilling requirement.*—This is a tropical highbush, this plant does not require chill hours for bud break.
*Canes.*—Moderately branched. Avg. 5-6 shoots per bush. Average 70-80 cm length, medium number of laterals.
*Young current-season-shoots.*—Yellow-Green group, color 144-A.
*One-year-old shoot branches color.*—Yellow-Green group, color 144-B.
*Mature cane color.*—Grayed-Orange group, color 165-C.
*Mature cane texture.*—Rough.
*Fruiting wood.*—Current season shoots.
*Internode length range.*—15-20 mm.
*Surface texture of new wood.*—Soft.
*Time of beginning of leaf bud burst.*—Budbreak occurs 15 days after pruning in Chao, Peru.
*Time of beginning of flowering.*—85-90 days after planting or pruning in Chao, Peru.
*Date of 50% open flowers.*—90-110 days after planting or pruning in Chao, Peru.
*Time of beginning of fruit ripening.*—Fruit ripening begins 147 days after planting or pruning.
*Disease resistance/susceptibility.*—None claimed.

Foliage:

*Young, newly expanded leaf color.*—Yellow-Green group, color 146-A.
*Leaf arrangement.*—Alternate.
*Mature, fully expanded leaves.*—Upper surface: Green group, color N137-A. Lower surface: Green group, color N138-C.
*Leaf margins.*—Serrate.
*Leaf venation.*—Pinnate.
*Leaf shape.*—Ovate.
*Leaf length.*—48-50 mm, average 49 mm.
*Leaf width.*—37-39 mm, average 38 mm.
*Leaf apices.*—Acuminate.
*Leaf bases.*—Acute.
*Vein and petiole coloration.*—Yellow-Green group, color 145-A.
*Petiole length.*—2.96 mm.
*Petiole diameter.*—2.74 mm.
*Evergreen.*—This variety is evergreen and keep its leaves during entire year.
*Fall leaf color.*—Does not apply for this genotype since it keeps leaves year round.

Leaf dimensions:

*Overall shape.*—Ovate.
*Length.*—48-50 mm, average 49 mm.
*Width.*—37-39 mm, average 38 mm.
*Leaf margins.*—Serrate.
*Leaf surface.*—Smooth.

Leaf buds:

*Shape.*—Round.
*Length.*—10.88 mm.
*Width.*—9.11 mm.
*Color.*—Greyed-Orange group, color 174-A.

Flower buds:

*Shape.*—Round.
*Length.*—10.88 mm.
*Width.*—9.11 mm.
*Color.*—Greyed-Orange group, color 174-A.

Flower:

*Flower shape.*—Urceolate.
*Flower bud number per lateral.*—5-12 flower buds.
*Flowers per cluster.*—3-6 flowers.
*Flower fragrance.*—Light floral.
*Corolla color.*—White group, color 8-D.
*Corolla length.*—12.72 mm.
*Corolla width.*—6 mm.
*Corolla aperture width.*—4.26 mm.
*Corolla texture.*—Smooth.
*Flower peduncle length.*—9.46 mm.
*Peduncle diameter.*—1.84 mm.
*Peduncle texture.*—Smooth.
*Peduncle color.*—Green group color, 139-D.
*Flower pedicel length.*—9.46 mm.
*Pedicel diameter.*—1.84 mm.
*Pedicel texture.*—Smooth.
*Pedicel color.*—Green group color, 139-D.
*Calyx (with sepals).*—7.5 mm.
*Calyx color.*—Green group color 143-B.
*Stamen length.*—7.36 mm.
*Stamen number per flower.*—11.
*Stamen filament color.*—Yellow-Green group color 149-D.
*Style.*—10.2 mm.
*Style color.*—Yellow-Green group, color 144-D.
*Ovary color.*—Yellow-Green group, color 147-B.

*Anther length.*—4.06 mm.
*Anther number.*—11.
*Anther color.*—White group, color 155-D.

Pollen:

*Abundance.*—Medium.
*Color.*—Yellow group, color 8-D.

Fruit:

*Date of* 50% *maturity.*—240 days after planting or pruning in Chao, Peru.
*Duration of ripening.*—Ripening period can last 200-210 days in Chao, Peru.
*Yield.*—3-3.5 kg per plant, two years old plant.
*Cluster density.*—Loose.
*Immature fruit color.*—Green group, color 143-C.
*Berry color with wax.*—Violet-Blue group, color 98-D.
*Berry color with wax removed.*—Greyed-Purple group, color N 186-A.
*Berry flesh color.*—Yellow-Green group, color 145-C.
*Berry surface wax abundance.*—High.
*Berry weight.*—4-5 g in Chao, Peru.
*Berry size diameter.*—22-25 mm, in Chao, Peru.
*Berry height.*—17 mm, in Chao, Peru.
*Berry width.*—25 mm, in Chao, Peru.
*Aspect* (*H/W*).—Ratio high/width 1.5.
*Berry shape.*—Oblate.
*Average number of fruits per cluster.*—5-7 fruits.
*Detachment force.*—Low.
*Self-fruitfulness.*—Fair, cross pollination may be desirable for maximum yield and fruit size.
*Fruit stem scar.*—5.7 mm diameter.
*Calyx.*—Six lobes with pronounced ridges.
*Calyx diameter.*—11.91 mm.
*Calyx depth.*—4.5 mm.
*Berry firmness.*—Firm 200-250 gf/mm (78-83 shore).
*Berry sweetness.*—High, 12.5-13° brix.
*Berry acidity.*—Medium to low titratable acidity, 0.7-0.8%.
*Berry flavor and texture.*—Good blueberry flavor, balanced sugar, and acidity.
*Storage ability.*—Good, 4-6 weeks in cold storage.
*Suitability for mechanical harvesting.*—Not tested.

Seed:

*Seed abundance in fruit.*—Medium.
*Seed color.*—Greyed-Orange group, color N167-A.
*Seed dry weight.*—0.4 mg.
*Seed size.*—1.73 mm length.

Possible typical Market uses: Mainly fresh market.

What is claimed is:

1. A new and distinct cultivar of Blueberry plant named 'PE2103' as described and shown herein.

* * * * *